(12) United States Patent
Mahajan et al.

(10) Patent No.: US 8,747,402 B2
(45) Date of Patent: Jun. 10, 2014

(54) ELECTRICAL CONDUCTIVITY PROBES FOR MEASURING ATTRIBUTES OF TISSUE

(75) Inventors: Roop L. Mahajan, Blacksburg, VA (US); Ming Yi, Beijing (CN); Ronald J. Podhajsky, Boulder, CO (US); Hrishikesh V. Panchawagh, Rochester, NY (US)

(73) Assignee: Covidien LP, Mansfield, MA (US)

( * ) Notice: Subject to any disclaimer, the term of this patent is extended or adjusted under 35 U.S.C. 154(b) by 57 days.

(21) Appl. No.: 13/351,553

(22) Filed: Jan. 17, 2012

(65) Prior Publication Data
US 2012/0116242 A1    May 10, 2012

Related U.S. Application Data

(60) Continuation of application No. 13/098,199, filed on Apr. 29, 2011, now Pat. No. 8,156,632, which is a division of application No. 12/016,754, filed on Jan. 18, 2008, now Pat. No. 7,951,144.

(60) Provisional application No. 60/881,238, filed on Jan. 19, 2007.

(51) Int. Cl.
*A61B 18/18* (2006.01)
(52) U.S. Cl.
USPC ........................................................ 606/41
(58) Field of Classification Search
USPC ........................................................ 606/41
See application file for complete search history.

(56) References Cited

U.S. PATENT DOCUMENTS

| | | |
|---|---|---|
| D223,367 S | 4/1972 | Kountz |
| 4,038,975 A | 8/1977 | Vrana et al. |
| 4,291,708 A | 9/1981 | Frei et al. |
| D263,020 S | 2/1982 | Rau, III |
| D266,842 S | 11/1982 | Villers et al. |
| D278,306 S | 4/1985 | McIntosh |
| 4,537,203 A | 8/1985 | Machida |
| 4,617,939 A | 10/1986 | Brown et al. |
| 4,719,441 A | 1/1988 | Horn |
| 4,729,385 A | 3/1988 | Juncosa et al. |

(Continued)

FOREIGN PATENT DOCUMENTS

| | | |
|---|---|---|
| CN | 1103807 | 6/1995 |
| DE | 390937 | 3/1924 |

(Continued)

OTHER PUBLICATIONS

U.S. Appl. No. 08/136,098, filed Oct. 14, 1993, Roger A. Stern.

(Continued)

*Primary Examiner* — Lisa Caputo
*Assistant Examiner* — Jonathan Dunlap (57) ABSTRACT

According to the present disclosure, a system for sensing attributes of tissue in at least one direction is provided. The system includes a thermal conductivity probe having a sensor configured to measure thermal conductivity in the target tissue in at least one direction, and an electrical conductivity probe having a sensor configured to measure electrical conductivity in the target tissue in at least one direction, a power supply operatively coupled to the thermal conductivity probe and being configured to supply power to the thermal conductivity probe, an impedance analyzer operatively coupled to the electrical conductivity probe, and a computer operatively coupled to at least one of the power supply, the multimeter and the impedance analyzer.

5 Claims, 7 Drawing Sheets

(56) References Cited

U.S. PATENT DOCUMENTS

| | | | |
|---|---|---|---|
| D295,893 S | 5/1988 | Sharkany et al. | |
| D295,894 S | 5/1988 | Sharkany et al. | |
| 4,902,138 A * | 2/1990 | Goeldner et al. | 374/44 |
| 4,955,383 A | 9/1990 | Faupel | |
| 4,960,109 A | 10/1990 | Lele | |
| 4,966,158 A | 10/1990 | Honma et al. | |
| 5,035,514 A | 7/1991 | Newman | |
| 5,184,620 A | 2/1993 | Cudahy et al. | |
| 5,184,624 A | 2/1993 | Brown et al. | |
| 5,217,014 A | 6/1993 | Hahn et al. | |
| 5,320,101 A | 6/1994 | Faupel et al. | |
| 5,353,802 A | 10/1994 | Ollman | |
| D354,218 S | 1/1995 | Van de Peer | |
| 5,630,426 A | 5/1997 | Eggers et al. | |
| 5,704,355 A | 1/1998 | Bridges | |
| 5,800,350 A | 9/1998 | Coppleson et al. | |
| 5,904,709 A | 5/1999 | Arndt et al. | |
| 5,959,241 A * | 9/1999 | Sriram et al. | 136/228 |
| 6,026,323 A | 2/2000 | Skladnev et al. | |
| D424,693 S | 5/2000 | Pruter | |
| D424,694 S | 5/2000 | Tetzlaff et al. | |
| D425,201 S | 5/2000 | Tetzlaff et al. | |
| 6,190,378 B1 | 2/2001 | Jarvinen | |
| 6,241,725 B1 | 6/2001 | Cosman | |
| D449,886 S | 10/2001 | Tetzlaff et al. | |
| D457,958 S | 5/2002 | Dycus et al. | |
| D457,959 S | 5/2002 | Tetzlaff et al. | |
| 6,467,951 B1 * | 10/2002 | Ghoshal | 374/45 |
| 6,524,308 B1 | 2/2003 | Muller et al. | |
| 6,668,230 B2 | 12/2003 | Mansky et al. | |
| D487,039 S | 2/2004 | Webster et al. | |
| D496,997 S | 10/2004 | Dycus et al. | |
| D499,181 S | 11/2004 | Dycus et al. | |
| 6,845,264 B1 | 1/2005 | Skladnev et al. | |
| D525,361 S | 7/2006 | Hushka | |
| D531,311 S | 10/2006 | Guerra et al. | |
| D533,942 S | 12/2006 | Kerr et al. | |
| D535,027 S | 1/2007 | James et al. | |
| D541,418 S | 4/2007 | Schechter et al. | |
| D541,938 S | 5/2007 | Kerr et al | |
| D564,662 S | 3/2008 | Moses et al. | |
| D576,932 S | 9/2008 | Strehler | |
| D594,736 S | 6/2009 | Esjunin | |
| D594,737 S | 6/2009 | Kelly et al. | |
| D606,203 S | 12/2009 | Husheer et al. | |
| D613,412 S | 4/2010 | DeCarlo | |
| D634,010 S | 3/2011 | DeCarlo | |
| 2002/0173731 A1 | 11/2002 | Martin et al. | |
| 2003/0097130 A1 | 5/2003 | Muller et al. | |
| 2004/0015162 A1 | 1/2004 | McGaffigan | |
| 2004/0037343 A1 | 2/2004 | Tanaka et al. | |
| 2005/0090881 A1 | 4/2005 | Frank et al. | |
| 2005/0124975 A1* | 6/2005 | Law | 604/522 |
| 2005/0282284 A1* | 12/2005 | Rubinsky et al. | 435/459 |
| 2007/0049915 A1 | 3/2007 | Haemmerich et al. | |
| 2007/0060921 A1 | 3/2007 | Janssen et al. | |
| 2008/0025366 A1 | 1/2008 | McBurney | |
| 2008/0161797 A1 | 7/2008 | Wang et al. | |
| 2008/0177199 A1 | 7/2008 | Podhajsky | |
| 2008/0294041 A1* | 11/2008 | Kassab | 600/433 |
| 2010/0118916 A1* | 5/2010 | Thomsen, III | 374/179 |
| 2011/0118721 A1 | 5/2011 | Brannan | |
| 2011/0118730 A1 | 5/2011 | DeCarlo | |
| 2011/0118731 A1 | 5/2011 | Ladtkow | |
| 2011/0152853 A1 | 6/2011 | Manley et al. | |
| 2011/0172659 A1 | 7/2011 | Brannan | |
| 2011/0184403 A1 | 7/2011 | Brannan | |
| 2011/0190754 A1 | 8/2011 | Kim et al. | |
| 2011/0196362 A1 | 8/2011 | Rossetto | |
| 2011/0203104 A1 | 8/2011 | Mahajan et al. | |
| 2011/0208177 A1 | 8/2011 | Brannan | |
| 2011/0208180 A1 | 8/2011 | Brannan | |
| 2011/0208184 A1 | 8/2011 | Brannan | |
| 2011/0213351 A1 | 9/2011 | Lee et al. | |
| 2011/0213352 A1 | 9/2011 | Lee et al. | |
| 2011/0213353 A1 | 9/2011 | Lee et al. | |
| 2011/0218527 A1 | 9/2011 | Prakash et al. | |
| 2011/0224504 A1 | 9/2011 | Ladtkow et al. | |
| 2011/0238053 A1 | 9/2011 | Brannan et al. | |
| 2011/0238054 A1 | 9/2011 | Kim et al. | |
| 2011/0238055 A1 | 9/2011 | Kim et al. | |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 37 11 511 | 6/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10310765 | 9/2004 |
| DE | 10328514 | 3/2005 |
| DE | 10 2004 022206 | 12/2005 |
| DE | 102004022206 | 12/2005 |
| DE | 20 2005 015147 | 2/2006 |
| DE | 202005015147 | 3/2006 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 0 882 955 | 12/1998 |
| EP | 1 159 926 | 5/2001 |
| EP | 0 648 515 | 4/2003 |
| EP | 1 462 065 | 9/2004 |
| FR | 179 607 | 11/1906 |
| FR | 1 275 415 | 10/1961 |
| FR | 1 347 865 | 11/1963 |
| FR | 2 235 669 | 1/1975 |
| FR | 2 276 027 | 1/1976 |
| FR | 2 313 708 | 12/1976 |
| FR | 2 502 935 | 10/1982 |
| FR | 2 517 953 | 6/1983 |
| FR | 2 573 301 | 5/1986 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |

(56) References Cited

FOREIGN PATENT DOCUMENTS

| | | |
|---|---|---|
| JP | 08252263 | 10/1996 |
| JP | 09000492 | 1/1997 |
| JP | 09010223 | 1/1997 |
| JP | 11244298 | 9/1999 |
| JP | 2000342599 | 12/2000 |
| JP | 2000350732 | 12/2000 |
| JP | 2001003776 | 1/2001 |
| JP | 2001008944 | 1/2001 |
| JP | 2001029356 | 2/2001 |
| JP | 2001037775 | 2/2001 |
| JP | 2001128990 | 5/2001 |
| JP | 2001231870 | 8/2001 |
| JP | 2008142467 | 6/2008 |
| SU | 166452 | 11/1964 |
| SU | 401367 | 11/1974 |
| SU | 727201 | 4/1980 |
| WO | WO 99/44520 | 9/1999 |
| WO | WO 00/54682 | 9/2000 |
| WO | WO 00/70333 | 11/2000 |
| WO | WO 2004/052182 | 6/2004 |
| WO | WO 2007/100559 | 9/2007 |
| WO | WO 2010/035831 | 4/2010 |

OTHER PUBLICATIONS

U.S. Appl. No. 08/483,742, filed Jun. 7, 1995, Roger A. Stern.
U.S. Appl. No. 12/861,333, filed Aug. 23, 2010, Joseph D. Brannan.
U.S. Appl. No. 12/944,951, filed Nov. 12, 2010, Joseph D. Brannan.
U.S. Appl. No. 12/977,390, filed Dec. 23, 2010, Joseph D. Brannan.
U.S. Appl. No. 12/977,415, filed Dec. 23, 2010, Joseph D. Brannan.
U.S. Appl. No. 12/985,124, filed Jan. 5, 2011, Joseph D. Brannan.
U.S. Appl. No. 12/985,136, filed Jan. 5, 2011, Joseph D. Brannan.
U.S. Appl. No. 12/985,155, filed Jan. 5, 2011, Joseph D. Brannan.
U.S. Appl. No. 12/985,179, filed Jan. 5, 2011, Joseph D. Brannan.
U.S. Appl. No. 13/020,562, filed Feb. 3, 2011, Joseph D. Brannan.
U.S. Appl. No. 13/020,664, filed Feb. 3, 2011, Kenlyn S. Bonn.
U.S. Appl. No. 13/024,041, filed Feb. 9, 2011, Joseph D. Brannan.
U.S. Appl. No. 13/029,521, filed Feb. 17, 2011, Joseph D. Brannan.
U.S. Appl. No. 13/029,594, filed Feb. 17, 2011, Joseph D. Brannan.
U.S. Appl. No. 13/043,665, filed Mar. 9, 2011, Richard A. Willyard.
U.S. Appl. No. 13/043,694, filed Mar. 9, 2011, Richard A. Willyard.
U.S. Appl. No. 13/050,729, filed Mar. 17, 2011, Casey M. Ladtkow.
U.S. Appl. No. 13/083,185, filed Apr. 8, 2011, Arnold V. DeCarlo.
U.S. Appl. No. 13/083,256, filed Apr. 8, 2011, Joseph D. Brannan.
U.S. Appl. No. 13/113,736, filed May 23, 2011, Ladtkow et al.
U.S. Appl. No. 13/118,929, filed May 31, 2011, Bonn et al.
U.S. Appl. No. 13/206,075, filed Aug. 9, 2011, Lee et al.
U.S. Appl. No. 13/236,997, filed Sep. 20, 2011, Behnke II, et al.
U.S. Appl. No. 13/237,068, filed Sep. 20, 2011, Behnke II, et al.
U.S. Appl. No. 13/237,187, filed Sep. 20, 2011, Behnke II, et al.
U.S. Appl. No. 13/237,342, filed Sep. 20, 2011, Behnke II, et al.
U.S. Appl. No. 13/237,488, filed Sep. 20, 2011, Behnke II, et al.
U.S. Appl. No. 13/267,369, filed Oct. 6, 2011, Prakash et al.
U.S. Appl. No. 13/268,143, filed Oct. 7, 2011, Kenlyn S. Bonn.
U.S. Appl. No. 13/281,605, filed Oct. 26, 201, Prakash et al.
U.S. Appl. No. 13/290,462, filed Nov. 7, 2011, Kenlyn S. Bonn.
U.S. Appl. No. 13/298,461, filed Nov. 17, 2011, Buysse et al.
U.S. Appl. No. 13/344,753, filed Jan. 6, 2012, Lee et al.
U.S. Appl. No. 13/343,788, filed Jan. 5, 2012, William O. Reid Jr.
U.S. Appl. No. 13/343,798, filed Jan. 5, 2012, William O. Reid Jr.
U.S. Appl. No. 13/344,790, filed Jan. 6, 2012, Lee et al.
U.S. Appl. No. 13/351,463, filed Jan. 17, 2012, Smith et al.
U.S. Appl. No. 13/358,129, filed Jan. 25, 2012, Joseph D. Brannan.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic ® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure™ " Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw•Hill, vol. 1 1 1, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of " Radiofrequency Lesions in the Dorsal Root Entry Zone Neurosurgery 15:(1984), pp. 945-950.
Crawford et al., "Use of the LigaSure™ Vessel Sealing System in Urologic Cancer Surger" Grand Rounds in Urology 1999, vol. I, Issue 4, pp. 1 0-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.

(56) References Cited

OTHER PUBLICATIONS

Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Humphries Jr. et al., "Finite•Element Codes to Model Electrical Heating and Non•LInear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4: No. 1, pp. 307-320.
Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol., BME-31, No. 1, Jan. 1984, pp. 28-37.
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1 st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General, Gynecologic, Urologic, and Laparaoscopic Surgery. Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.

M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/1977).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001)71.9 pp. 538-540.
Sigel et al., "The Mechanism of Blood Vessel Closure by High Frequency Electrocoagulation" Surgery Gynecology & Obstetrics, Oct. 1965 pp. 823-831.

(56) References Cited

OTHER PUBLICATIONS

Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Perctitaneous Microwave Coagulation Therapy for Small Hepatocellular Carcinoma," Cancer 74(3):817.825.
Urologix, Inc.-Medical Professionals: Targis™ Technology (Date Unknown). "Overcoming the Challenge" located at: <http://www.urologix.com!medicaUtechnology.html > Nov. 18, 1999; 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Aug. 4, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001016.8 dated Jan. 4, 2008.
European Search Report EP 08001019 dated Sep. 23, 2008.
European Search Report EP 08004974.5 dated Apr. 6, 2011.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.

(56) References Cited

OTHER PUBLICATIONS

European Search Report EP 08007924.7 partial dated Aug. 17, 2010.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09012389.4 dated Jul. 6, 2010.
European Search Report EP 09151621 dated Jun. 18, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.
European Search Report EP 09704429.1 extended dated Mar. 23, 2011.
European Search Report EP 10001767.2 extended dated Jun. 18, 2010.
European Search Report EP 10004950.1 extended dated Jul. 2, 2010.
European Search Report EP 10004951.9 extended dated Jul. 2, 2010.
European Search Report EP 10005533.4 extended dated Sep. 24, 2010.
European Search Report EP 10005534.2 extended dated Sep. 17, 2010.
European Search Report EP 10006373.4 extended dated Nov. 11, 2010.
European Search Report EP 10008139.7 extended dated Nov. 30, 2010.
European Search Report EP 10008140.5 extended dated Dec. 28, 2010.
European Search Report EP 10008533.1 extended dated Dec. 20, 2010.
European Search Report EP 10008850.9 extended dated Nov. 30, 2010.
European Search Report EP 10009731.0 extended dated Jan. 28, 2011.
European Search Report EP 10009732.8 extended dated Jan. 26, 2011.
European Search Report EP 10010943.8 extended dated Feb. 1, 2011.
European Search Report EP 10011750.6 extended dated Feb. 1, 2011.
European Search Report EP 10014042.5 extended dated Feb. 18, 2011.
European Search Report EP 10014080.5 extended dated Mar. 17, 2011.
European Search Report EP 10014081.3 extended dated Mar. 17, 2011.
European Search Report EP 10014705.7 extended dated Apr. 27, 2011.
European Search Report EP 10158944.8 extended dated Jun. 21, 2010.
European Search Report EP 10161596.1 extended dated Jul. 28, 2010.
European Search Report EP 10161722.3 extended dated Jun. 16, 2010.
European Search Report EP 10163235.4 dated Aug. 10, 2010.
European Search Report EP 10172634.7 dated Nov. 9, 2010.
European Search Report EP 10185413.1 dated Dec. 7, 2010.
European Search Report EP 10185413.1 dated Mar. 14, 2011.
European Search Report EP 10191321.8 dated Apr. 7, 2011.
European Search Report EP 11000548.5 extended dated Apr. 14, 2011.
European Search Report EP 11004942 dated Sep. 23, 2011.
European Search Report EP 11174318.3 dated Nov. 7, 2011.
International Search Report PCT/US97/05066 dated Jun. 24, 1997.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/USO4/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report PCT/US10/032796 dated Jul. 28, 2010.
European Search Report dated Nov. 7, 2013 in European Appln. No. 11176685.
European Search Report dated Nov. 7, 2013 in European Appln. No. 11176684.
European Search Report dated Sep. 23, 2008 in European Appln. No. 08001019.
European Search Report dated Apr. 1, 2008 in European Appln. No. 08001016.
Ming Yi and Al: "Micromachined Electrical 1-7 Conductivity Probe for RF Ablations of Tumors" Proceedings of the 2005 ASME International Mechanical Engineering Congress and Exposition, Nov. 5, 2005, Nov. 11, 2005, pp. 53-56, XP008156650, *abstract*, *p. 54, left-hand column, paragraphs 1, 2*, *figures 1, 2*.

\* cited by examiner

ELECTRICAL CONDUCTIVITY PROBES FOR MEASURING ATTRIBUTES OF TISSUE

CROSS-REFERENCE TO RELATED APPLICATION

The present application is continuation of U.S. patent application Ser. No. 13/098,199, filed on Apr. 29, 2011, published on Aug. 25, 2011 as U.S. Patent Application Publication No. US 2011/0203104 A1 by Mahajan et al., entitled "THERMAL AND ELECTRICAL CONDUCTIVITY PROBES AND METHODS OF MAKING THE SAME", now U.S. Pat. No. 8,156,612 issued on Apr. 17, 2012, which is a divisional of, and claims priority to, U.S. patent application Ser. No. 12/016,754, filed on Jan. 18, 2008, published as U.S. Patent Application Publication No. US 2008/0175299 A1 by Mahajan et al., entitled "THERMAL AND ELECTRICAL CONDUCTIVITY PROBES AND METHODS OF MAKING THE SAME", now U.S. Pat. No. 7,951,144 issued on May 31, 2011, which claims the benefit of and priority to U.S. Provisional Application Ser. No. 60/881,238, filed on Jan. 19, 2007, the entire content of each of which is incorporated herein by reference.

BACKGROUND

1. Technical Field

The present disclosure relates to electrosurgical instruments, systems and methods of making the same. More particularly, the present disclosure relates to conductivity probes for sensing directional attributes of tissue and methods of making the same.

2. Discussion of Related Art

It has been observed that biological tissue has different thermal and/or electrical conductivities in different directions.

Thermal conductivity of biological tissues is dependent on the particular type of biological tissue and on the composition of the biological tissue. Different biological tissues exhibit different and/or unique thermal conductivity based on factors such as tissue density, vascularization, age, direction and distance to major blood vessels, etc. Additionally, different biological tissues may exhibit a different and/or unique thermal conductivity in different directions.

Electrical conductivity is not only determined by tissue type and composition, but also by other externally applied physical and chemical influences during thermal treatment, such as, for example, temperature inducement and saline pretreatment.

Knowing the thermal and/or electrical conductivity of tissue may be used by a surgeon in a number of applications, including, but not limited to, predicting the effect of thermal treatment on given tissue, identifying the location and size of internal structures, and enhancing the resolution of traditional imaging devices.

SUMMARY

Accordingly, a need exists for thermal and electrical conductivity probes for sensing the directional attributes of tissue and methods of making the same.

A system for sensing attributes of tissue in at least one direction is provided. The system includes a thermal conductivity probe including a sensor configured to measure thermal conductivity in the target tissue in at least one direction, a power supply operatively connected to the thermal conductivity probe and being configured to supply power to the thermal conductivity probe, a multimeter operatively connected the thermal conductivity probe; an electrical conductivity probe including a sensor configured to measure electrical conductivity in the target tissue in at least one direction, an impedance analyzer to measure the tissue impedance (or equivalently electrical conductivity) and a computer operatively connected to at least one of the multimeter and impedance analyzer. In the system, the thermal conductivity probe and the electrical conductivity probe may be integrated into a single probe.

Also provided is a thermal conductivity probe for sensing directional attributes of tissue. The probe includes a body and a sensor operably connected to the body. The sensor includes a line heater having one or more resistive heating elements, a detector having one or more detector elements, and a substrate for supporting the line heater and the detector and to provide thermal conductivity contrast. The body of the probe may define a catheter configured for insertion into tissue. The pair of outer detector elements may form resistance temperature detector elements (RTD). The pair of inner heating elements may be substantially parallel. The probe may further include an array of sensors.

A method of making a thermal conductivity probe is also provided. The method includes providing an inert substrate, depositing a first layer on the substrate, depositing a second layer on the first layer, generating a first pattern in the first and second layers, generating a second pattern in the second layer, and depositing an insulative layer over the first and second layers. The first and second layers may be deposited using evaporation techniques. The first layer may be selected from the group consisting of titanium (Ti), titanium tungsten (TiW) and platinum (Pt). The second layer may be selected from the group consisting of gold (AU), iridium (Ir) and platinum-iridium (Pt—Ir). The first layer may measure about 50 nm thick. The second layer may measure about 500 nm thick. The first and second patterns may be generated using an etching technique.

In addition, an electrical conductivity probe for measuring attributes of tissue is provided. The probe includes a body and a sensor for sensing electrical conductivity. The sensor includes a pair of electrodes, a pair of bonding pads coupled to the pair of electrodes by a pair of electrical leads, and a substrate for supporting the electrodes, bonding pads and leads. The pair of electrodes may be parallel. The body of the probe may define a catheter configured for insertion into tissue.

The sensor may include insulating material at least partially overlying the pair of electrodes, and an exposed region formed in the insulation and associated with each electrode.

A method of making an electrical conductivity probe is also provided. The method includes providing a substrate, depositing an adhesive layer on the substrate, depositing a conductive layer on the adhesive layer, generating a pattern on the adhesive layer and the conductive layer, and depositing an insulating layer over the conductive layer and the pattern. The adhesive layer and conductive layer may be deposited using evaporation techniques. The pattern may define first and second electrodes. The adhesive layer may be selected from the group consisting of titanium (Ti), titanium tungsten (TiW) and platinum (Pt), and may measure about 30 nm thick. The conductive layer selected from the group consisting of gold (AU), iridium (Ir) and platinum-iridium (Pt—Ir), and may measure about 330 nm thick. The insulative layer may be spun onto the conductive layer and pattern.

DETAILED DESCRIPTION OF THE DRAWINGS

Embodiments of the present disclosure are disclosed herein with reference to the drawings, wherein.

DETAILED DESCRIPTION OF EMBODIMENTS

The devices, systems and methods of the present disclosure provide for the sensing of directional attributes of tissue in order to help in predicting and/or planning thermal therapy procedures. In the drawings and in the description which follows, the term "proximal", as is traditional, will refer to the end of the system, or component thereof, which is closest to the operator, and the term "distal" will refer to the end of the system, or component thereof, which is more remote from the operator.

As used herein, the term "thermal treatment" is understood to include and is not limited to radio-frequency (RF) treatment, laser treatment, microwave treatment and cryoablation treatment.

1. Sensing System

Figure 1:
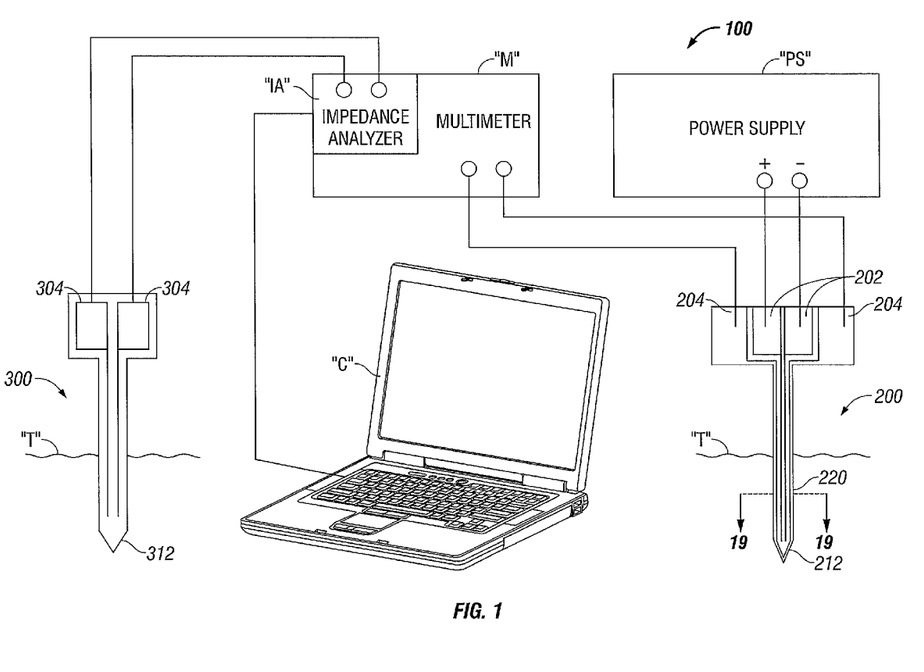
FIG. 1 is a schematic perspective view of a sensing system according to an embodiment of the present disclosure.

With reference to FIG. 1, in accordance with an embodiment of the present disclosure, a sensing system for sensing directional attributes of tissue is generally designated as 100. System 100 includes a thermal conductivity probe 200, power supply "PS" connected to or connectable to probe 200, a multimeter "M" connected to or connectable to probe 200, and a computer "C" connected to or connectable to multimeter "M". System 100 may further include an electrical conductivity probe 300 connected to an impedance analyzer "IA", or other suitable devices Impedance analyzer "IA" may be formed integral with multimeter "M", or may instead include a separate unit. Power supply "PS" may include any power source capable of providing constant power. For example, power supply "PS" may include a DC power source.

As seen in FIG. 1, thermal conductivity probe 200 includes a first pair of bonding pads 202 electrically connected to or electrically connectable to power supply "PS", and a second pair of bonding pads 204 electrically connected to or electrically connectable to multimeter "M". Electrical conductivity probe 300 may include a pair of bonding pads 304 electrically connected to or electrically connectable to impedance analyzer "IA".

2. Thermal Conductivity Probe

A micro thin-film thermal conductivity probe has been developed to measure thermal conductivity of biological tissues based on the principle of traditional hot-wire method. An embodiment of the design of the microprobe of the present disclosure includes a resistive line heating element on a substrate and a Resistance Temperature Detector (RTD) based temperature sensor.

Figure 2A:
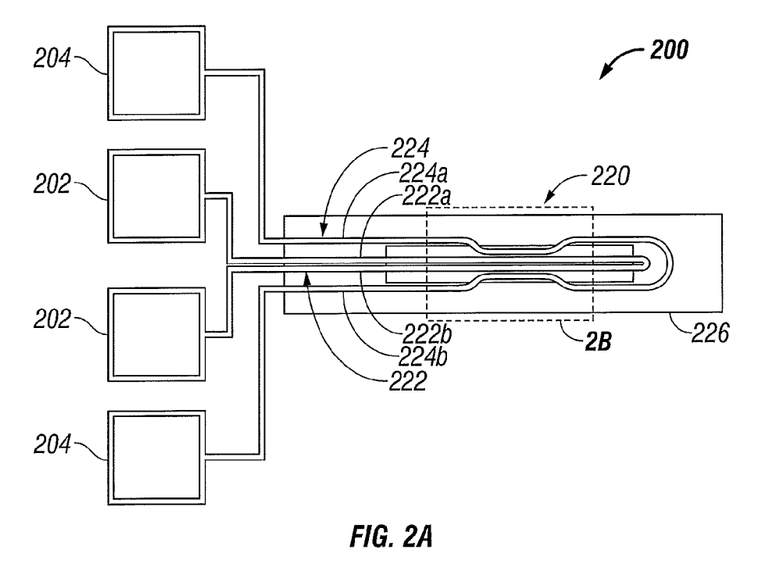
FIG. 2A is a schematic illustration of an embodiment of a micro thermal probe of the sensing system of FIG. 1.
Figure 2B:
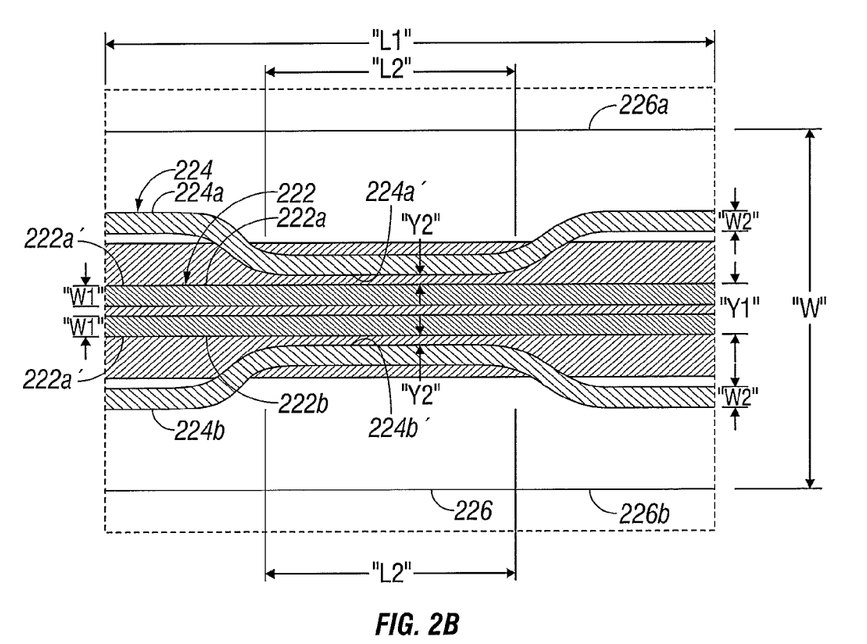
FIG. 2B is an enlarged view of the indicated area of detail 5 of FIG. 2A.

With continued reference to FIG. 1 and with reference to FIGS. 2A and 2B, a more detailed discussion of thermal conductivity probe 200 is provided. Probe 200 may be in the form of a needle, probe antenna or the like or any other suitable configuration. In one embodiment, probe 200 may include an elongate body 210, in the form of a catheter, defining a sharpened or pointed distal tip 212.

Probe 200 further includes a microprobe sensor 220 suitably secured to catheter 210. Microprobe sensor 220 may be disposed at least partially within catheter 210, on an outer surface of catheter 210, imbedded in the outer surface of catheter 210 and/or according to any other suitable method. As seen in FIGS. 2A and 2B, microprobe sensor 220 includes a line heating element 222 having a pair of resistive inner thin-film heating elements 222a, 222b, a detector element 224 having a pair of outer "resistance temperature detector" (RTD) elements 224a, 224b, and a substrate 226 for supporting heating elements 222a, 222b and RTD elements 224a, 224b. The substrate 226 defines a first lateral edge 226a and a second lateral edge 226b and defines a width "W" between the first lateral edge 226a and the second lateral edge 226b.

In one embodiment, line heating element 222 has a width "W1" of approximately 100 microns (μm) and a length "L1" of approximately 5000 microns (μm). Meanwhile, detector element 224 may have a width "W2" of approximately 100 μm and a length of approximately 1500 μm. The dimensions disclosed herein are representative, it is envisioned and within the scope of the present disclosure for the dimensions to have any suitable value, such as, for example, having lengths that are approximately 3.0 times greater than the lengths "L1", "L2" specified or having lengths that are approximately 0.2 times less than the lengths specified. The width "W" of the substrate 226 is greater than the widths "W1" and "W2". It is contemplated that the lengths selected, for example, may be chosen for optimal use in a specific target tissue, e.g., liver, lung, kidney, muscle, etc.

As best seen in FIG. 2B, heating elements 222a, 222b of line heating element 222 are substantially parallel to one another and are spaced a distance "Y1" from one another. Distance "Y1" may be approximately 100 μm. The first and second resistive heating elements 222a and 222b are disposed between the first and second detector elements 224a and 224b, respectively. Each heating element 222a, 222b is spaced apart from a respective RTD element 224a, 224b by a distance "Y2". The first and second detector elements 224a and 224b are disposed on the substrate substantially parallel to one another and each define an inner edge 224a' and 224b', respectively, along the length of the substrate 226. The first and second resistive heating elements 222a and 222b are disposed on the substrate substantially parallel to one another and each define an outer edge 222a', and 222b', respectively, along the length of the substrate 226. The first and second detector elements 224a and 224b are each disposed separately in an outer position with respect to, and closer to, the first and second lateral edges 226a, 226b defined by the substrate 226 as compared to the first and second resistive heating elements 222a, 222b, respectively. The first and second resistive heating elements 222a, 222b are each disposed separately in an inner position as compared to the first and second detector elements 224a and 224b and with respect to the first and second lateral edges 226a, 226b defined by the substrate 226, respectively. The first and second resistive heating elements 222a, 222b define the first width dimension "Y1" that characterizes the combined width of the first and second resistive heating elements 222a, 222b on the substrate 226 that is less than the second width dimension "W" defined by the distance between the first and second lateral edges 226a, 226b defined by the substrate 226. The distance "Y2" between the outer edges 222a', 222b' of the resistive heating elements 222a, 222b and the inner edges 224a', 224b' of the detector elements 224a, 224b each define a third width dimension that is distance "Y2". Distance "Y2" may be approximately 50 μm.

Figure 3:
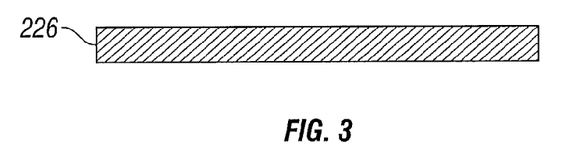
FIGS. 3-9 are schematic illustrations of exemplary steps in the fabrication of the micro thermal probe of FIGS. 2A and 2B.
Figure 4:
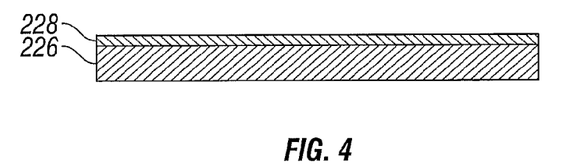
Figure 5:
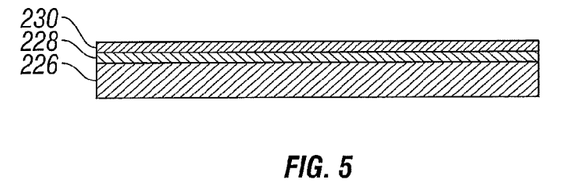

Turning now to FIGS. 3-9, a representative method of manufacturing microprobe sensor 220 is shown and described. The steps involved in the manufacture of microprobe sensor 220 include, as seen in FIG. 3, providing a substrate 226, e.g., glass, polyimide (kapton) or other polymeric substrate that is inert. In an embodiment, substrate 226 may have a thickness approximately equal to 1.0 millimeters (mm). Next, as seen in FIG. 4, a first layer 228 is deposited on substrate 226 using evaporation techniques or other suitable deposition techniques. First layer 228 may be fabricated from titanium (Ti) titanium tungsten (TiW), platinum (Pt) or other like materials, and may have a thickness of approximately 50 nanometers (nm). Next, as seen in FIG. 5, a second layer 230 is deposited on first layer 228 using evaporation techniques or other suitable deposition techniques. Second layer 230 may be fabricated from gold (Au), iridium (Ir), platinum-iridium alloy (Pt—Ir) or other like materials, and may have a thickness of approximately 500 nm. The dimensions of microprobe sensor 220 provided herein are merely representative, and may be made larger or smaller depending on the application. For example, microprobe sensor 220 may be reduced in size when configured for use with infants. In one exemplary embodiment, microprobe sensor 220 may include a substrate 226 having a thickness approximately equal to 300 μm to 1000 μm, and in a further embodiment approximately equal to 500 μm.

Figure 6:
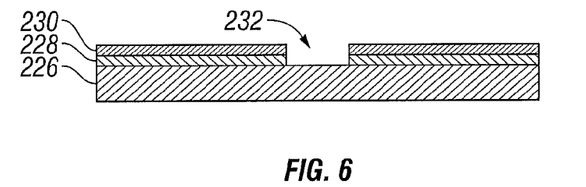
Figure 7:
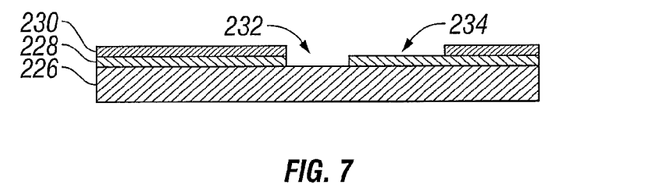

As seen in FIG. 6, suitable photolithography techniques or other suitable etching or removal techniques are used to generate a desired first pattern 232 in first and second layers 228, 230 by using a precision photomask (not shown). Next, as seen in FIG. 7, second layer 230 is etched, using photolithography techniques or other suitable etching or removal techniques, to create a second pattern 234 therein. In this manner, the heating elements and the RTD elements are defined.

Figure 8:
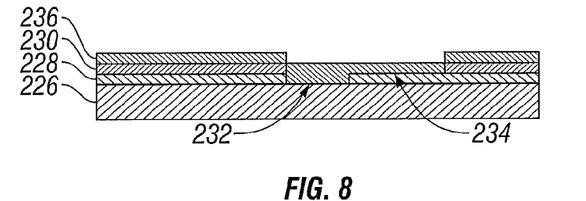
Figure 9:
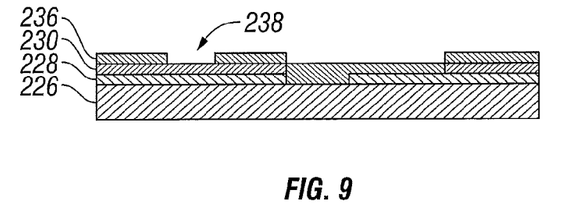

As seen in FIG. 8, an insulating layer 236 is deposited, i.e., spun onto, overtop first and second layers 228, 230 and first and second patterns 232, 234. Insulating layer 236 may comprise a dielectric layer of benzocyclobutane (BCB), silica (SiO2), parylene, polyimide, SU8, or other like materials. Insulating layer 236 functions to protect first and second layers 228, 230 from corrosive element in tissue, such as, for example, saline. As seen in FIG. 9, areas 238 are exposed in insulating layer 236 to define bonding pads 202, 204 and expose bonding pads 202, 204 for soldering or the like. Sensor 220 may further be coated with a hydrophilic or hydrophobic layer (not shown) for increasing the biocompatibility of sensor 220.

Wires (not shown) may be welded, soldered, ball bonded, epoxied, etc. to each bonding pad 202, 204 and microprobe sensor 220 may then be placed within elongate body 210 (see FIG. 1). A waterproof epoxy may be used to hold microprobe sensor 220 in place within elongate body 210 and to protect microprobe sensor 220.

3. Method of Using Thermal Conductivity Probe

With reference to FIGS. 1-2B, a representative method of using thermal conductivity probe 200, is provided. As seen in FIG. 1, with the first pair of bonding pads 202 electrically connected to power source "PS", and with the second pair of bonding pads 204 electrically connected to multimeter "M", thermal conductivity probe 200 may be used to determine the thermal conductivity of target tissue. The transient time response of heating elements 222a, 222b is dependent on a thermal conductivity of the medium surrounding microprobe sensor 220 and the substrate underlying microprobe sensor 220.

According to a method of the present disclosure, a 5V output, generated by power source "PS", is used to provide a constant current through heating elements 222a, 222b. A resistance change of the RTD elements 224a, 224b, due to the transient temperature elevation, is measured by multimeter "M", an impedance analyzer or the like. Computer "C" is used to monitor, record and acquire the data and/or readings generated by microprobe sensor 220.

The transient time response of the RTD elements 224a, 224b depends on the thermal conductivity of the surrounding medium and the substrate. A theoretical analysis of the transient conduction, for a configuration where the heater source is sandwiched between two materials (the substrate and the surrounding medium), shows that the composite thermal conductivity calculated from the temperature versus the logarithm of time response is simply an average of the thermal conductivity of the two materials.

The equation for the calculation is:

$$k = \frac{k_{tissue} + k_{substrate}}{2} = \frac{q''}{2\pi}\left(\frac{dT}{d\ln t}\right)^{-1}$$

k—is the calculated thermal conductivity;
$k_{tissue}$—is the thermal conductivity of the tested tissue;
$k_{substrate}$—is the thermal conductivity of the sensor substrate;
q"—is the heat flux produced by heating element;
T—is the temperature; and
t—is the time.

In use, catheter 210 is inserted into the target tissue "T" and microprobe sensor 220 is activated to determine the thermal conductivity of said target tissue. Thermal conductivity probe 200 is adapted to measure thermal conductance $K_{eff}$ as represented by the following equation, as commonly known in the field:

$$K_{eff} = K\left\{1 + \frac{n[(\rho c)_b \pi r_b^2 \overline{V} \cos\gamma]^2}{\sigma_\Delta K^2}\right\} + q_{met}$$

where:

$K_{eff}$—is the "effective" tissue conductance which is measured. $K_{eff}$ is the combination of conduction (due to intrinsic thermal conductivity) and convection (due to perfusion);

$K_{tissue}$—is tissue conductance in the absence of perfusion;

n—is the number of blood vessels;

p—in $(pc)_b$ is the density of blood;

c—in $(pc)_b$ is the specific heat of blood;

$r_b$—is vessel radius;

V—is the blood flow velocity vector within the vessel;

γ—is the relative angle between blood vessel direction and tissue temperature gradient;

$\sigma_\Delta$—is a shape factor term; and $q_{met}$—is metabolic heat generation.

S. Weinbaum and L. M. Jiji, "A new simplified equation for the effect of blood flow on local average tissue temperature," ASME J. Biomech. Eng. 107: 131-139, 1985.

4. Electrical Conductivity Probe

Figure 10A:
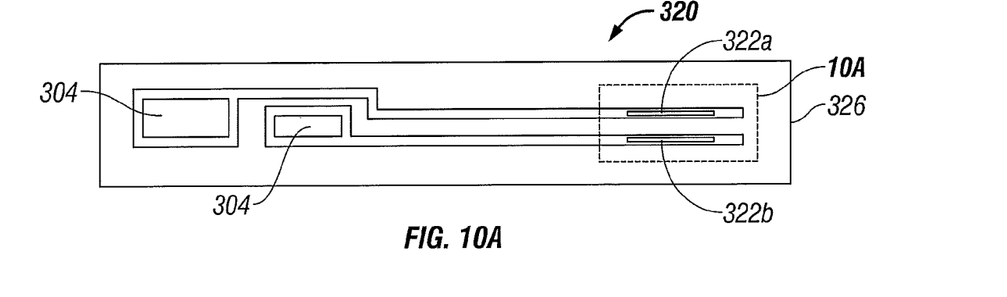
FIG. 10A is a schematic illustration of an embodiment of another electrical microprobe of the sensing system of FIG. 1.
Figure 10B:
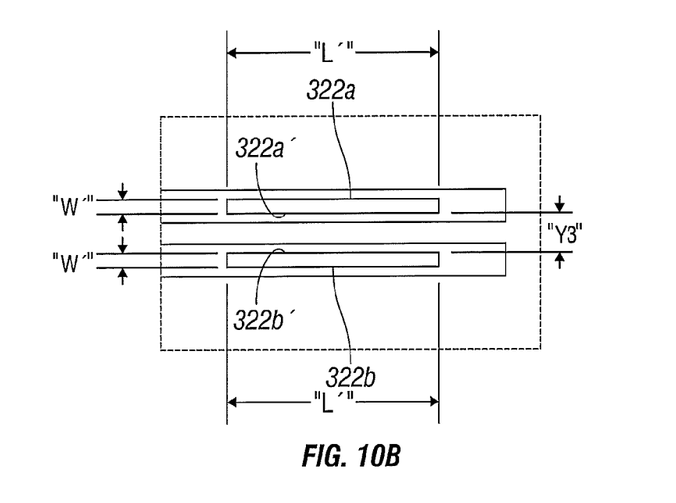
FIG. 10B is an enlarged view of the indicated area of detail of FIG. 10A.

With reference to FIG. 1 and with reference to FIGS. 10A and 10B, a more detailed discussion of electrical conductivity probe 300 is provided. Probe 300 may be in the form of a needle, probe antenna or the like or any suitable configuration. For example, probe 300 may include an elongate body 310, in the form of a catheter, defining a sharpened or pointed distal tip 312.

Probe 300 further includes a sensor 320 suitably secured to catheter 310. Sensor 320 may be disposed at least partially within catheter 310, on an outer surface of catheter 310, imbedded in the outer surface of catheter 310 and/or according to any other suitable.

As seen in FIGS. 10A and 10B, sensor 320 includes a pair of electrodes 322a, 322b defining a sensor area "SA", a pair of electrical leads 323a, 323b respectively connecting electrodes 322a, 322b to bonding pads 304, and a substrate 326 for supporting electrodes 322a, 322b, leads 323a, 323b and bonding pads 304.

In one embodiment, each electrode 322a, 322b has a width "W3" of approximately 150 nm and a length "L3" of approximately 2,000 μm. While the dimensions disclosed herein are representative or exemplary, it is envisioned and within the scope of the present disclosure for the dimensions to have any suitable value, such as, for example, having lengths that are approximately 3.0 times greater than the lengths specified or having lengths that are approximately 0.2 times less than the lengths specified. It is contemplated that the lengths selected, for example, may be chosen for optimal use in a specific target tissue, e.g., liver, lung, kidney, muscle, etc. As best seen in FIGS. 10A and 10B, electrodes 322a, 322b are substantially parallel to one another and are spaced a distance "Y3" from one another. Distance "Y3" may be approximately 300 μm.

Figure 11:
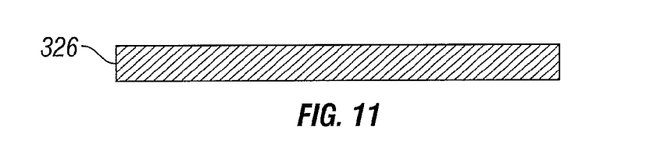
FIGS. 11-16 are schematic illustrations of exemplary steps in the fabrication of the electrical microprobe of FIGS. 10A and 10B.
Figure 12:
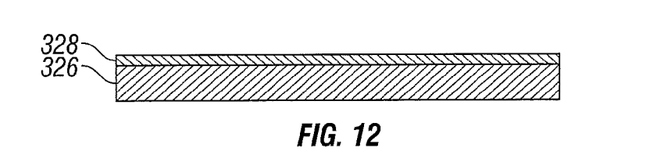
Figure 13:
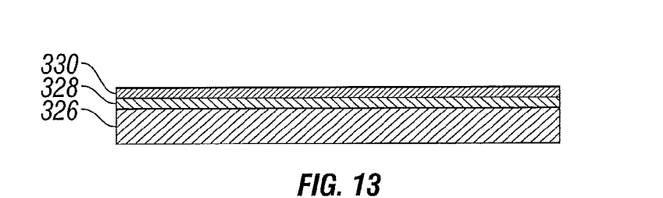

Turning now to FIGS. 11-16, an exemplary method of manufacturing sensor 320 is shown and described. The steps involved in the manufacture of sensor 320 include, as seen in FIG. 11, providing a substrate 326, e.g., a polyimide or other suitable substrate that is inert. In an embodiment, substrate 326 may have a thickness between approximately 300 μm and 1,000 μm, and in a further embodiment may be approximately 500 μm. Next, as seen in FIG. 12, an adhesive layer 328 is deposited on substrate 326 using suitable deposition by evaporation techniques or other suitable deposition and/or evaporation techniques. Adhesive layer 328 may be fabricated from titanium (Ti) titanium tungsten (TiW), platinum (Pt) or other like materials, and may have a thickness of approximately 30 nm. Next, as seen in FIG. 13, a conductive layer 330 is deposited on adhesive layer 228 using suitable deposition by evaporation techniques or other suitable deposition and/or evaporation techniques. Conductive layer 330 may be fabricated from gold (Au), iridium (Ir), platinum-iridium alloy (Pt—Ir) or other like materials, and may have a thickness of approximately 300 nm. The dimensions of microprobe sensor 320 provided herein are merely representative, and may be made larger or smaller depending on the application.

Figure 14:
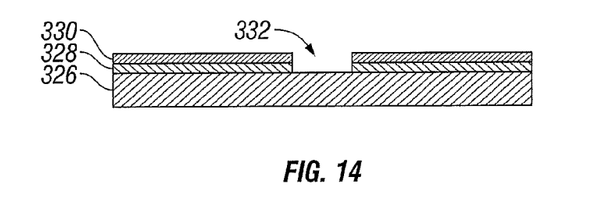
Figure 15:
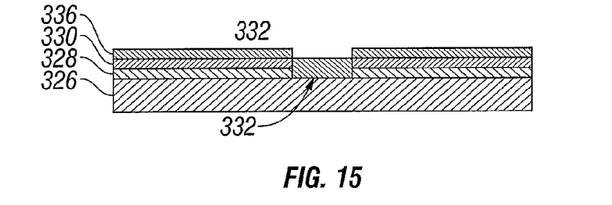
Figure 16:
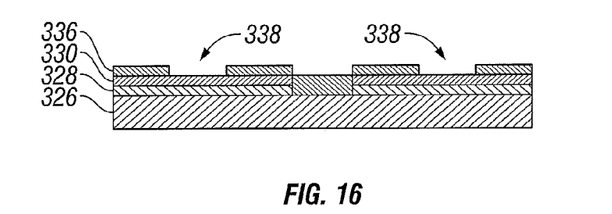
Figure 17:
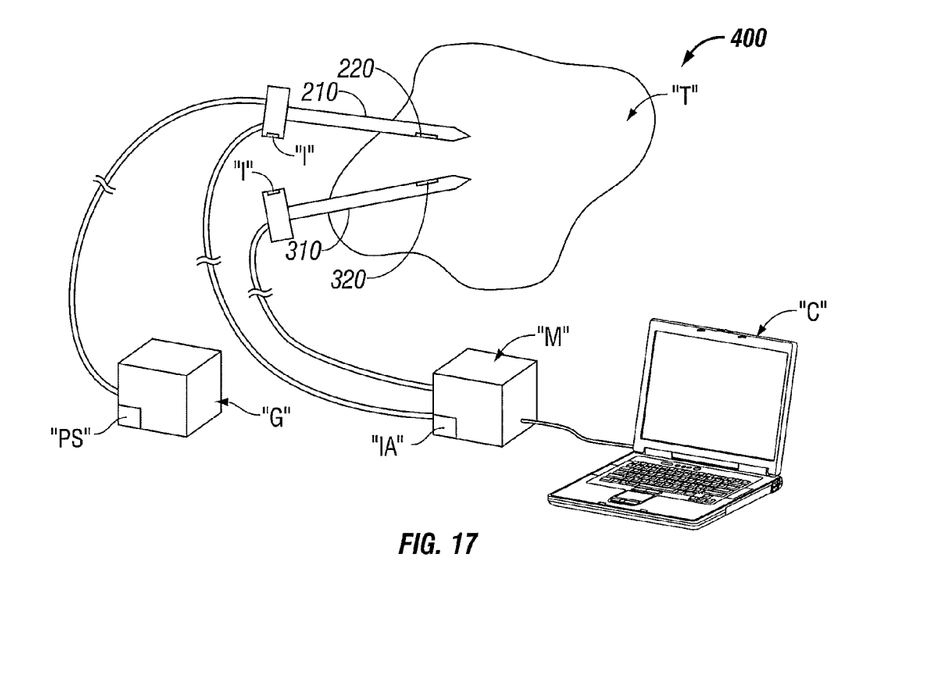
FIG. 17 is a schematic illustration of an electrosurgical system including the sensing system of FIG. 1, shown in operative association with a target tissue.
Figure 18:
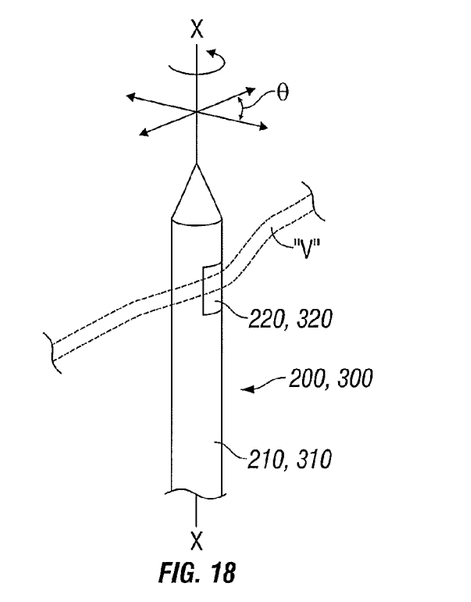
FIG. 18 is a perspective view of a distal end of an electrical microprobe of the present disclosure.

As seen in FIG. 14, suitable photolithography and/or etching techniques are used to generate a desired pattern 332 defining first and second electrodes 322a, 322b. Next, as seen in FIG. 15, an insulating layer 336 is deposited, e.g., spun onto, overtop conductive layer 330 and pattern 332. Insulating layer 336 may comprise a dielectric layer of benzocyclobutane (BCB), silica ($SiO_2$), parylene C or other like materials. Insulating layer 336 functions to protect conductive layer 330 from corrosive element in tissue, such as, for example, saline. As seen in FIG. 16, areas 338 are patterned into insulating layer 336 to define first and second electrodes 322a, 322b and bonding pads 304 and to expose bonding pads 304 for soldering or the like.

Wires (not shown) may be welded, soldered, ball bonded, epoxied, etc. to each bonding pad 304 and sensor 320 may then be paced within elongate body 310 (see FIG. 1). A waterproof epoxy may be used to hold sensor 320 in place within elongate body 310 and to protect sensor 320. Sensor 320 may further be coated with a hydrophilic or hydrophobic layer (not shown) for increasing the biocompatibility of sensor 320.

5. Method of Using Electrical Conductivity Probe

With reference to FIGS. 1, 10A and 10B, a representative method of using electrical conductivity probe 300, is provided. As seen in FIG. 1, with the pair of bonding pads 304 electrically connected to multimeter "M" or impedance analyzer, electrical conductivity probe 300 may be used to determine the electrical conductivity of target tissue prior to an electrosurgical procedure.

According to a method of the present disclosure, a 500 kHz output frequency, generated by multimeter "M", is used to provide electrosurgical energy to electrodes 322a, 322b. A return pad or electrode (not shown) is employed to complete a circuit with electrodes 322a, 322b, via tissue "T". The computer "C" is used to monitor, record and acquire the data and/or readings generated by sensor 320.

Before use, the impedance values by the micro electrical probe are calibrated in different salinity levels against the standard four-electrode probe which provides a direct measure of the electrical conductivity. A calibration curve is generated that relate the impedance value given by the micro electrical probe to the electrical conductivity measured by the standard four-electrode probe at different salinity levels. The electrical conductivity can be calculated by comparing the impedance value with the calibration curve. In use, catheter 310 is inserted into the target tissue "T" and sensor 320 is activated to determine the electrical conductivity of said target tissue "T".

Figure 19:
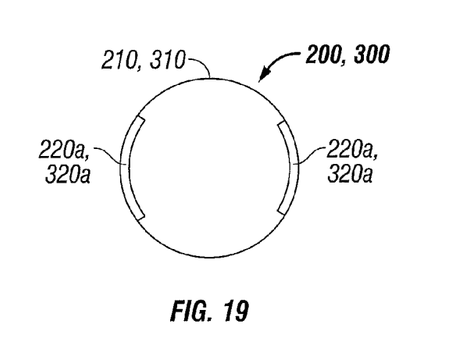
FIG. 19 is a transverse, cross-sectional view of an electrical microprobe as taken through 19-19 of FIG. 1.
Figure 20:
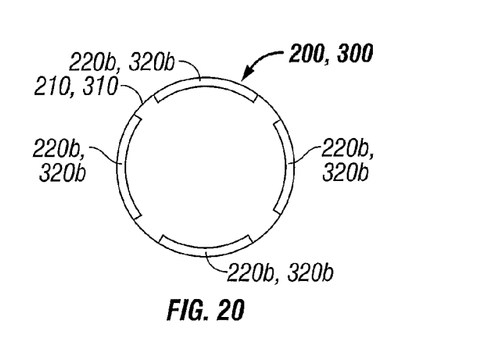
FIG. 20 is a transverse, cross-sectional view of another electrical microprobe as taken through 19-19 of FIG. 1.

While each of the above embodiments illustrates a single sensor 220, 320 associated with each respective device 200, 300, in accordance with the present disclosure, devices 200, 300 may employ or include at least two or multiple sensors 220, 320 disposed around a circumference thereof. As seen in FIG. 19, each of devices 200, 300 may include a pair of sensors 220a, 320a disposed on opposed sides thereof, or as seen in FIG. 20, each of devices 200, 300 may include a sensors 220b, 320b disposed at 90° angles relative to one another.

Figure 21:
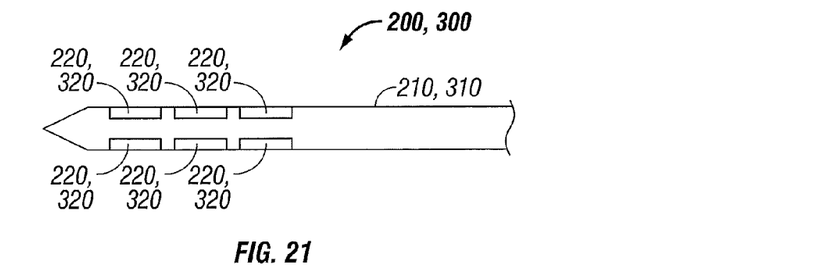
FIG. 21 is a schematic illustration of a distal end of an electrical microprobe according to yet another embodiment of the present disclosure.
Figure 22:
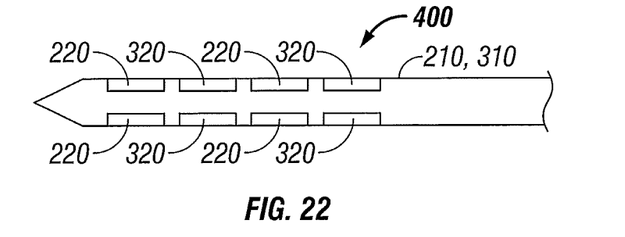
FIG. 22 is a schematic illustration of a distal end of an integrated electrical and thermal microprobe according to still another embodiment of the present disclosure.

As seen in FIG. 21, sensors 220, 320 may be disposed at different axial locations along a length of respective catheter 210, 310. As seen in FIG. 22, sensors 220, 320 may be provided on a single electrosurgical device 400. In this manner, electrosurgical device 400 will be capable of measuring and/or capturing both the values of thermal conductivity and electrical conductivity of target tissue "T".

According to an alternate embodiment of the present disclosure, as seen in FIG. 22, sensors 220, 320 may be incorporated into or otherwise associated with a thermal treatment device 500, in the form of an ablation needle, probe, antenna or the like. Thermal treatment device 500 defines an electrically exposed distal tip 502 configured and adapted to deliver therapeutic energy to target tissue, according to any suitable known method in the art. Distal tip 502 extends from an insulated shaft 504 or the like.

Figure 23:
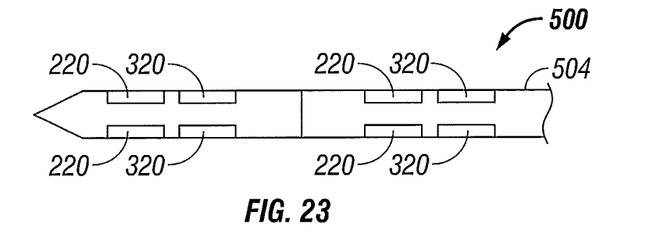
FIG. 23 is a schematic illustration of a distal end of an electrical ablation device according to an embodiment of the present disclosure.

As seen in FIG. 23, sensors 220, 320 may be provided along and/or incorporated into distal tip 502 and/or provided along and/or incorporated into shaft 504. The particular arrangement, location and orientation of sensors 220, 320 relative to one another and relative to distal tip 502 and 504 may be selected or chosen as needed and/or desired.

Figure 24:
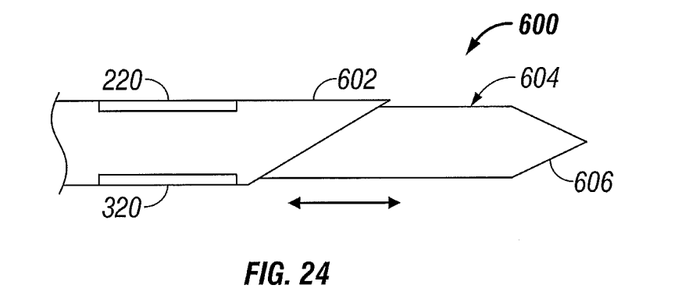
FIG. 24 is a schematic illustration of a distal end of an electrosurgical device according to another embodiment of the present disclosure.
Figure 25:
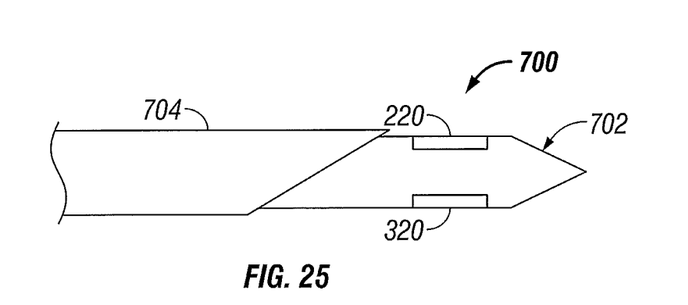
FIG. 25 is a schematic illustration of a distal end of an electrosurgical device according to still another embodiment of the present disclosure.

As seen in FIG. 24, sensors 220, 320 may be provided along and/or incorporated into an outer tube 602 of a thermal treatment device 600. In this manner, outer tube 602 of thermal treatment device 600 may be retracted relative to shaft 604, or in the alternative, shaft 604 may be extended relative to outer tube 602, to expose an operational end 606 of thermal treatment device 600. In an alternate embodiment, as seen in FIG. 25, sensors 220, 320 may be provided along and/or incorporated into a shaft 702 of a thermal treatment device 700. In this manner, shaft 702 of thermal treatment device 700 may be extended relative to an operational outer tube 704, thereby exposing sensors 220, 320. In a further embodiment, operational outer tube 704 may be replaced with an energy delivery needle or the like for delivering therapeutic energy to surrounding tissue and thermal treatment device 700 may be extended relative to energy delivery needle 704.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

What is claimed is:

1. An electrical conductivity probe for measuring attributes of tissue, the probe comprising:
    a body; and
    a sensor for sensing electrical conductivity, wherein the sensor includes:
        a pair of electrodes disposed in parallel relation to one another;
        a pair of bonding pads coupled to the pair of electrodes by a pair of electrical leads; and
        a substrate for supporting the electrodes, bonding pads and leads, the electrodes each having a width dimension of approximately 150 microns ($\mu$m) and a length dimension ranging from approximately 200 microns ($\mu$m) to approximately 6000 microns ($\mu$m).

2. The probe of claim 1, wherein the body defines a catheter configured for insertion into tissue.

3. The probe of claim 1, wherein the sensor includes insulating material at least partially overlying the pair of electrodes, and an exposed region formed in the insulation and associated with each electrode.

4. The probe of claim 1, wherein the electrodes having a length dimension of approximately 2000 microns ($\mu$m).

5. The probe of claim 1, wherein the electrodes are spaced apart a distance of approximately 300 microns ($\mu$m).

\* \* \* \* \*